United States Patent
Tu

[11] Patent Number: 6,068,645
[45] Date of Patent: May 30, 2000

[54] FILTER SYSTEM AND METHODS FOR REMOVING BLOOD CLOTS AND BIOLOGICAL MATERIAL

[76] Inventor: Hosheng Tu, 2151 Palermo, Tustin, Calif. 92782

[21] Appl. No.: 09/326,815

[22] Filed: Jun. 7, 1999

[51] Int. Cl.[7] .......................... A61M 29/00; A61B 17/00
[52] U.S. Cl. ............................................ 606/200; 606/159
[58] Field of Search ................. 606/1, 7, 14, 17, 606/15, 16, 159, 200, 198

[56] References Cited

U.S. PATENT DOCUMENTS

| | | |
|---|---|---|
| 5,053,008 | 10/1991 | Bajaj ...................................... 606/200 |
| 5,713,853 | 2/1998 | Clark et al. .............................. 606/200 |
| 5,725,550 | 3/1998 | Nadal . |
| 5,893,869 | 4/1999 | Barnhart et al. . |
| 5,902,263 | 5/1999 | Patterson et al. . |

*Primary Examiner*—Michael Buiz
*Assistant Examiner*—William W. Lewis

[57] ABSTRACT

A filter system and methods for removing blood clots and/or emboli by collecting them in a filtering element and thermally treating same by delivering therapeutic energy through a bipolar electrode members to the collected blood clots and emboli. Other alternate energy may also be applied to the collected blood clots and emboli for treating them in situ.

18 Claims, 8 Drawing Sheets

FILTER SYSTEM AND METHODS FOR REMOVING BLOOD CLOTS AND BIOLOGICAL MATERIAL

TECHNICAL FIELD OF THE INVENTION

The present invention generally relates to improved medical system and methods for treating blood vessels, and more particularly, to such a filter system and methods for removing blood clots and emboli by collecting them in a filtering element and thermally treat same by delivering therapeutic RF energy through a bipolar electrode means to the collected blood clots and emboli. Other alternate energy may also be applied to the collected blood clots, emboli or biological debris for treating them in situ.

BACKGROUND OF THE INVENTION

Blood vessel embolism is referred to hereby as an obstruction of a blood vessel by blood clots, emboli, or other foreign substances. This is a major cause of mortality and morbidity in the United States, particularly when blood vessel embolism occurs in a pulmonary vein or a coronary artery. To prevent embolism from occurring, patients are commonly treated with anticoagulants or with thrombolytic agents. In some situations, reliance on drugs may be inappropriate where a patient has high risk of internal bleeding or sensitive to a particular drug.

A blood filtration device has been widely used to collect and remove the blood clots, emboli and foreign substance from a blood vessel. Nadal in U.S. Pat. No. 5,725,550 discloses a blood filtration unit that is to be implanted in a vessel of a patient's body, especially for the purposes of retaining blood clots. The implanted filtration unit, either permanently or temporarily, continues to collect blood clots or emboli. The collected junk, including blood emboli, blood clots, debris and any foreign substance, should be removed and disposed of out of the body. Alternately, the junk should be treated in situ so that the treated blood emboli or clots are so small that they do not pose any harm to the blood vessel or to the patient. A permanently implanted filter system may need frequent junk removal when the accumulation of clots or emboli is excessive.

Barnhart et al. in U.S. Pat. No. 5,893,869 discloses a percutaneous filter system for providing temporary filtering of emboli from the blood. The filter system comprises a deployable filtering element to trap the blood junk that includes blood emboli, blood clots, debris and any foreign substance. When the filtering element is so deployed within a blood vessel, the junks entrapped within the filtering element are funneled toward a venting lumen and are aspirated or otherwise removed therethrough.

The conventional filtering devices, such as the one disclosed in U.S. Pat. No. 5,893,869, employ a lumen passageway for removing the blood emboli or clots. There are several disadvantages related to the system having an aspiring lumen passageway. First, the size of a delivery catheter incorporating an aspiring passageway is bulkier than a catheter without such a luminal passageway. A bulky catheter cannot be used in a small blood vessel. This becomes a more critical issue, because blood clots are mostly often associated with a small blood vessel. Secondly, blood is simultaneously aspired along with the blood clots or emboli through a removing passageway. An external filtering unit may be required to filter the aspired blood and return the filtered blood back to the patient. A blood salvage unit is particularly useful for returning the autologous blood to the same patient because of fear of cross-contamination from donated blood. By salvaging the autologous blood, anticoagulant is added to the filtered blood to prevent undesired blood coagulation or blood clotting.

Therefore, there is a clinical need to treat the blood emboli or blood clots in situ. This is particularly beneficial for the implanted blood filtering system to reduce the accumulation of the blood clots inside the filtering element. The treated clots or emboli can generally be returned to the circulatory system without further post-treatment in situ.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency energy can be applied to a biological material or debris through a bipolar electrode means, wherein the biological debris may comprise blood clots, blood emboli, foreign biological substance and the like. Other alternate energy or mechanical means may also be used in treating the entrapped biological debris.

SUMMARY OF THE INVENTION

In general, it is an object of the present invention to provide a method and an improved filtering apparatus for removing and treating blood emboli, blood clots, foreign biological substance, and the like. It is another object of the present invention to provide a method and an apparatus for collecting and treating blood emboli/clots in situ. It is still another object to provide a filter system that employs radiofrequency energy, other alternate energy, or mechanical means to treat the collected blood emboli. The radiofrequency energy can be provided through a bipolar electrode means, which comprises a first electrode with a forwarding electrical conductor from an external radiofrequency generator and a second electrode with a returning electrical conductor to said radiofrequency generator. The collected blood clots, blood emboli, and other foreign biological substance are appropriately funneled to between the two electrodes. When radiofrequency energy is applied to the bipolar electrode means, the collected blood clots, blood emboli, other foreign biological substance and the like are thermally treated for reduction of the size so that they can safely be returned to the blood stream. The "biological debris" is defined in his invention as including blood clots, blood emboli, emboli, loosen biological debris, and the like. The "biological vessel" is defined in this invention as including blood vessel, arterial vessel, venous vessel, and other body vessels or fluid channels.

Briefly, heat is generated by supplying a suitable energy source to an apparatus, which comprises an electrode means for transmitting RF current, in contact with biological debris through a bipolar electrode means. A suitable energy source may consist of radiofrequency energy, microwave energy, ultrasonic energy, alternating current energy, or laser energy. The energy can be applied to the treating means and subsequently delivered to the biological debris through the electrode means. The "debris treating means" in this invention may include electrode means for RF energy, transducer means for ultrasound energy, antenna means for microwave energy, and fiber optics for laser energy delivery.

In a particular case of radiofrequency therapy, a DIP (dispersive indifferent pad) type pad, that contacts the biological tissue or debris, is connected to the Indifferent Electrode Connector on the RF generator. Therefore, the RF energy delivery becomes effective when a close circuit from a RF generator through a biological tissue and returning to the RF generator is formed. When using an alternating current outlet, the generator should be grounded to avoid electrical interference. Heat is controlled by the power of the RF current delivered and by the delivery duration. The standard RF current generator means and its applications through the electrode means to a biological tissue are well known to one who is skilled in the art.

In one embodiment, a filter system within a biological vessel comprises a delivery catheter having a distal section, a distal end, a proximal end, and at least one lumen extending between the distal end and the proximal end, wherein the at least one lumen has at least one opening at the distal end of the delivery catheter. A handle is attached to the proximal end of the delivery catheter, wherein the handle has a cavity. A retractable elongate element is located inside the at least one lumen of the delivery catheter, said elongate element having a distal end and a proximal end. The filter system further comprises filter device means for filtering fluid within the biological vessel, wherein the filter device means comprises a debris treatment means for treating biological debris and a filtering element, the filter device means being mounted at the distal end of the elongate element, the filtering element being made of shape memory material and being formed to have a pre-disposed shape which, when said filtering element is deployed, defines a filtering channel that extends radially outwardly so that a cross-sectional area of the biological vessel is essentially covered by a periphery of said filtering channel. The filter system further comprises a filter deployment means mounted on the handle, the filter deployment means being attached to the proximal end of the elongate element, wherein the elongate element is pushed distally, at a deployed state of the filter deployment means, so that the filtering element is fully deployed out of the at least one lumen of the delivery catheter and so that the biological debris are trapped within the filtering element.

The filtering element of the filter system may form a generally frutoconical shape. The debris treating means may be selected from the group consisting of an ultrasound transducer, a plurality of laser fiber optics, a microwave antenna, a mechanical compressor, and a mechanical cutter. The filtering channel defined by said filtering element may be at least as large as or larger than a diameter of the biological vessel. The filtering element may be shaped either concave or convex with reference to a central axial line when the filtering element is deployed. This is to accommodate the biological fluid flow direction, either along with or against the delivery catheter from the proximal end to the distal end.

The filter system may further comprise at least one temperature sensor for measuring temperature of the trapped biological debris, wherein the temperature sensor is preferably disposed at close proximity of the bipolar electrode means or the debris treatment means. In another embodiment, the filter system may further comprise a temperature controller, wherein the temperature measured from the at least one temperature sensor is relayed to said temperature controller, the temperature controller being adapted for effecting RF current delivery to the bipolar electrode means. When RF current is used, the RF current varies within the range of 50 to 2,000 kHz. In an alternate embodiment, an exterior surface of the filtering element is electrically non-conductive.

The method for filtering and treating emboli from blood within a blood vessel comprises (a) introducing a delivery catheter into the blood vessel; (b) advancing a distal end of the delivery catheter to a desired location within the blood vessel; and (c) advancing a filtering element relative to the delivery catheter so that the filtering element deploys out of at least one lumen of the delivery catheter and expands into its pre-disposed shape within the blood vessel for trapping emboli.

In a preferred embodiment of the method for filtering and treating emboli from blood within a blood vessel, the emboli treatment means is selected from the group consisting of a radiofrequency bipolar electrode, an ultrasound transducer, a plurality of laser fiber optics, a microwave antenna, a mechanical compressor, and a mechanical cutter.

The method and medical apparatus of the present invention has several significant advantages over other known systems or techniques to filter and treat the biological debris, which includes blood clots, blood emboli, emboli, loosen biological debris, and the like. In particular, the apparatus system comprising a filtering element and a debris treatment means, using RF current as a heat source in this invention results in a more efficient filtering effect, which is highly desirable in its intended applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 8, what is shown is a preferred embodiment of the filter system, comprising applying radiofrequency energy, other alternate energy, or mechanical means to treat the entrapped biological debris collected in a filtering element.

Figure 1:
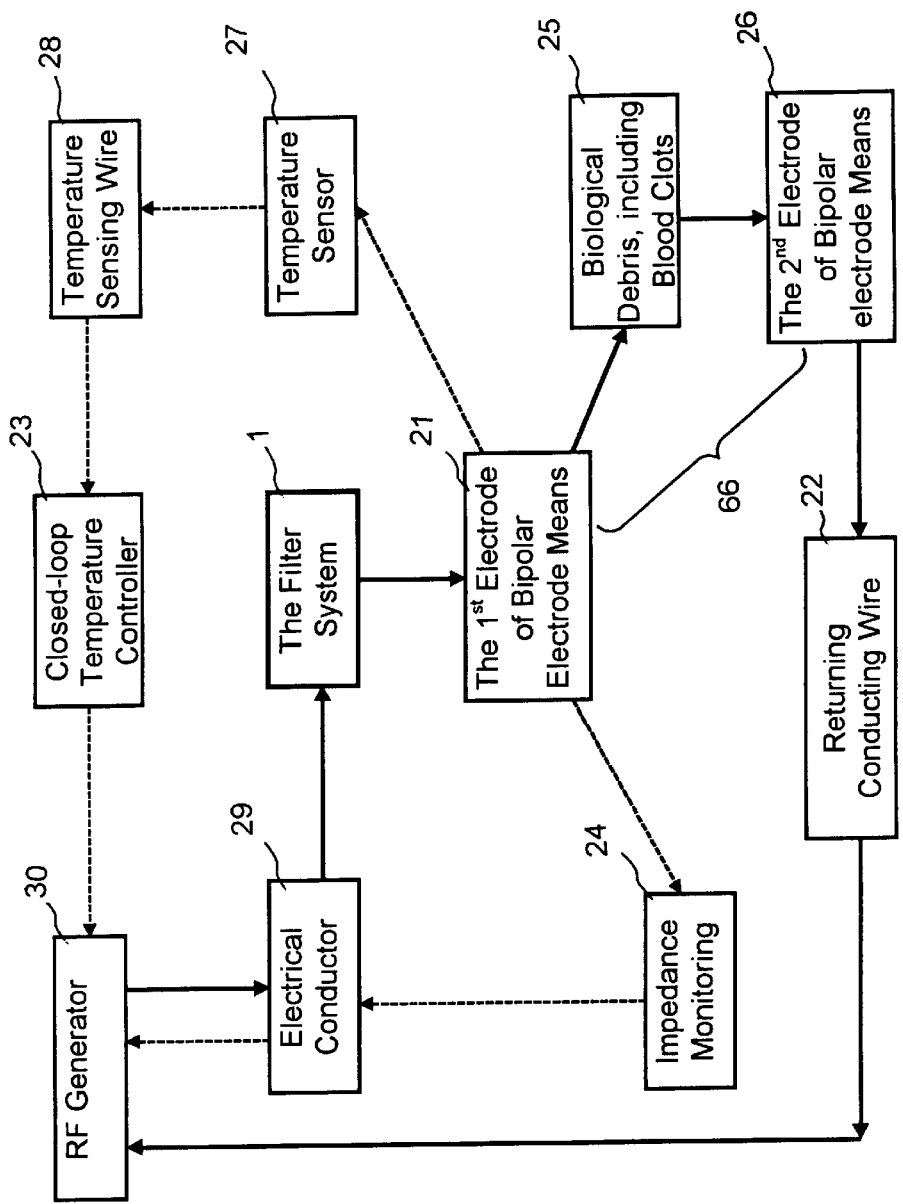
FIG. 1 is a schematic diagram of a RF treatment method in relation to the biological debris or clots through a filter system having a bipolar electrode debris treatment means.

FIG. 1 shows a schematic diagram of a RF treatment method in relation to the biological debris or clots through a filter system in a patient having a bipolar electrode debris treatment means. In one embodiment using RF therapy, a RF current generator 30 is connected to a first electrode of a bipolar electrode means 66 on a delivery catheter in a filter system. RF current is delivered to the bipolar electrode means 66 through a forwarding electrical conductor 29 to a first electrode 21 of the bipolar electrode means 66, and wherein the RF current returns from a second electrode 26 of the bipolar electrode means 66 through a returning electrical conductor 22 to the RF current generator 30 to form a complete circuit.

In a conventional circuit setup, the second electrode 26 functions as a PID pad. The first electrode 21 and the second electrode 26 of the bipolar electrode means 66 is to contact the blood clot or biological debris 25. Therefore, the RF energy delivery becomes effective when a close circuit from a RF generator through biological debris 25 and returning to the RF generator is formed. Impedance 24 measured from the debris contact is to ensure good debris contact for treatment, otherwise the RF current is cutoff when the impedance is unreasonably high. A temperature sensor 27 is also used to measure the debris temperature and is relayed through a temperature sensing wire 28 and a closed-loop temperature controller 23 for controlling the ablative energy delivered. Heat is controlled by the power of the RF current delivered and by the delivery duration.

Figure 2:
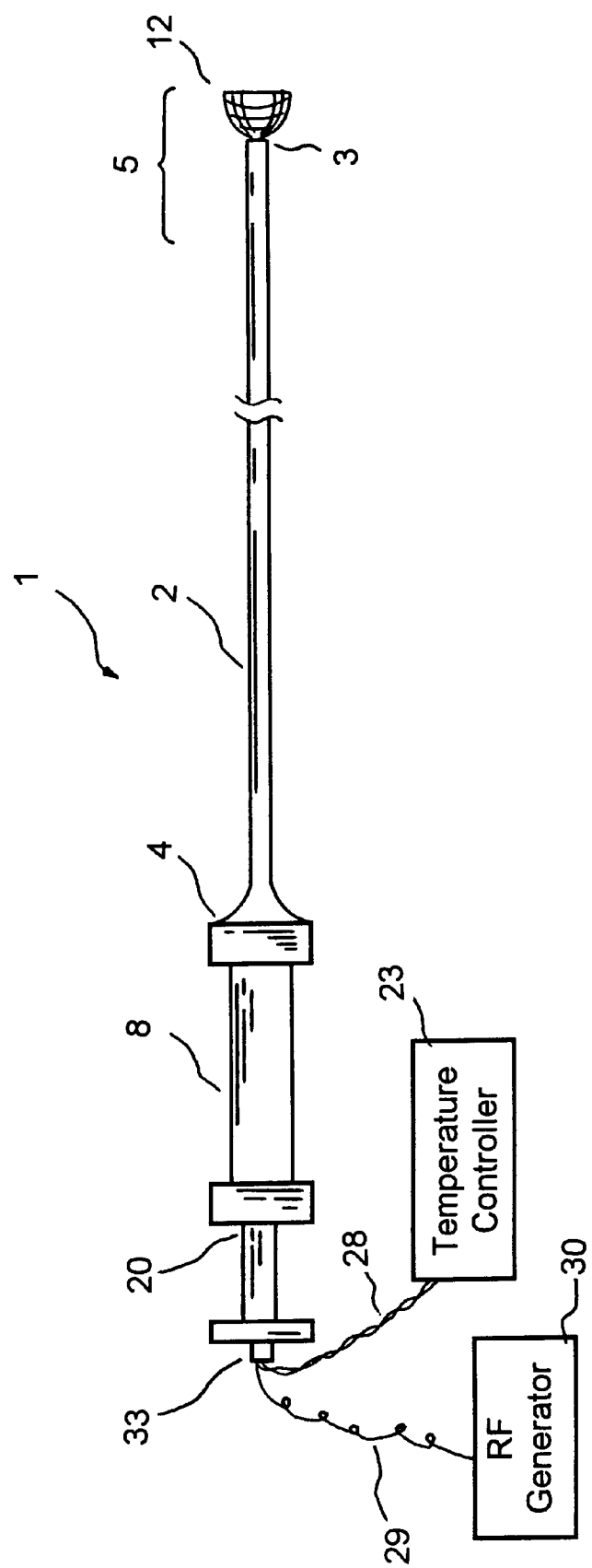
FIG. 2 is an overall view of a filter system having a delivery catheter comprising filter device means, constructed in accordance to the principles of the present invention.

As shown in FIG. 2, a filter system 1 comprises a delivery catheter 2 having a distal section 5, a distal end 3, a proximal end 4, and at least one lumen 6 extending between the distal end 3 and the proximal end 4, wherein the at least one lumen 6 has at least one opening 7 at the distal end 3 of the delivery catheter 2. A handle 8 is attached to the proximal end 4 of the delivery catheter 2, wherein the handle 8 has a cavity. A retractable elongate element 9 is located inside the at least one lumen 6 of the delivery catheter 2. The elongate element 9 has a distal end 10 and a proximal end. The delivery catheter comprises filter device means 67 for filtering fluid within the biological vessel, wherein the filter device means 67 comprises a bipolar electrode means 66 or other debris treatment means and a filtering element 12, the filter device means being mounted at the distal end 10 of the elongate element 9, the filtering element being made of shape memory material and being formed to have a pre-disposed shape which, when said filtering element 12 is deployed, defines a filtering channel that extends radially outwardly so that a cross-sectional area of the biological vessel is essentially covered by a periphery of said filtering channel.

Figure 3:
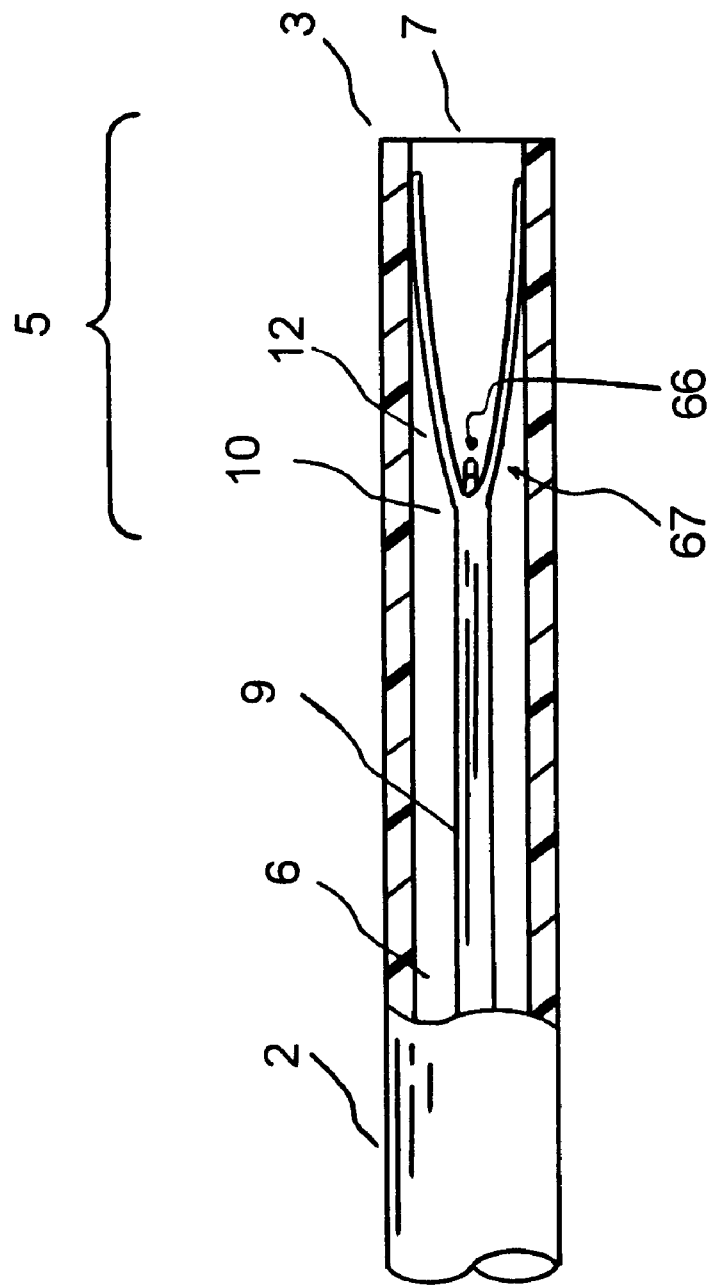
FIG. 3 is a cross-sectional view of the distal end portion of the delivery catheter, having a deployable filter element positioned within the lumen of the delivery catheter at a retracted, non-deployed state.

FIG. 3 shows a cross-sectional view of the distal end portion of the delivery catheter 2, having a deployable filter element positioned within the lumen 6 of the delivery catheter at a retracted, non-deployed state. Under a non-deployed state, the deployable filter device means 67, including a filter element 12 and a bipolar electrode means 66, is retracted inside the lumen 6 of the distal end portion 5 of the delivery catheter 2. The opening 7 at the distal end 3 of the delivery catheter 2 is for the retraction and deployment of the filter device means 67.

Figure 4:
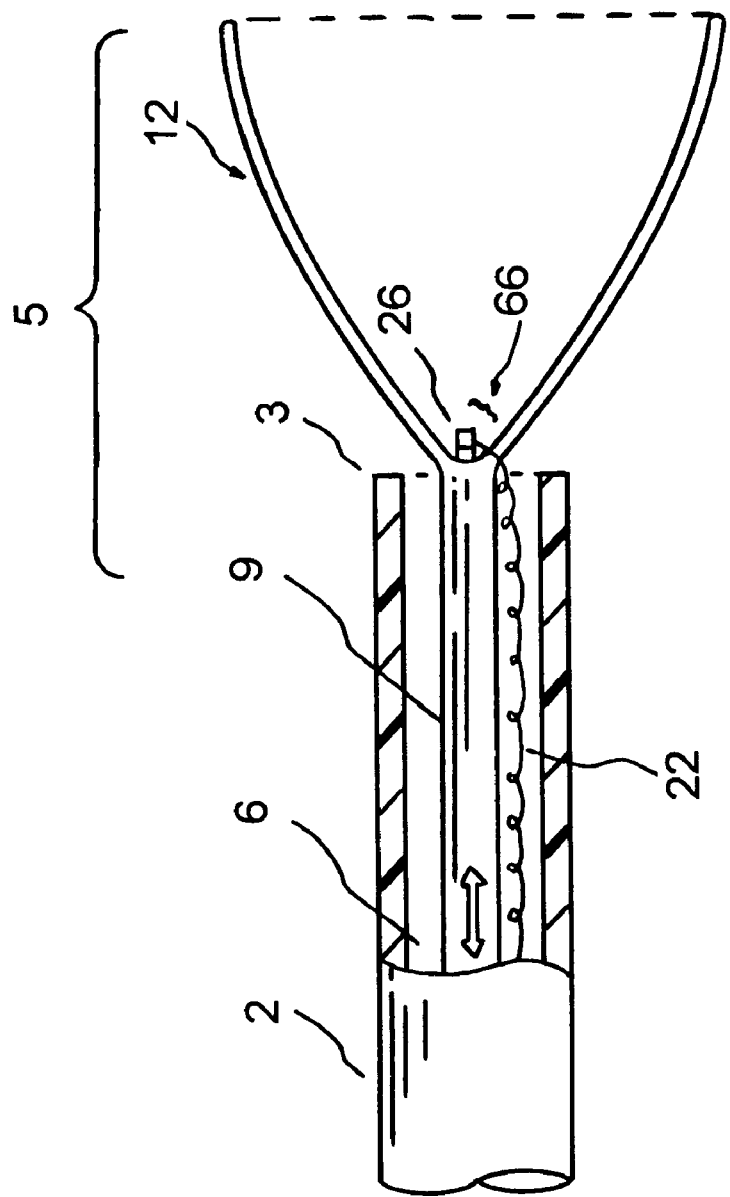
FIG. 4 is a cross-sectional view of the distal end portion of a preferred delivery catheter, having a deployable filter element at a deployed state.

FIG. 4 shows a cross-sectional view of the distal end portion of a preferred delivery catheter 2, having a deployable filter element 12 at a deployed state. The filter device means 67 for filtering fluid within the biological vessel comprises a bipolar electrode means 66 and a filtering element 12, the filter device means 67 being mounted at the distal end 10 of the elongate element 9, the filtering element 12 being made of shape memory material and being formed to have a pre-disposed shape. When said filtering element 12 is deployed, the filtering element defines a filtering channel that extends radially outwardly so that a cross-sectional area of the biological vessel is essentially covered by a periphery 14 of said filtering channel.

A filter deployment means 20 is mounted on the handle 8, the filter deployment means 20 being attached to the proximal end of the elongate element 9, wherein the elongate element is pushed distally, at a deployed state of the filter deployment means 20, so that the filtering element 12 is fully deployed out of the at least one lumen 6 of the delivery catheter 2 and so that biological debris 25 are trapped within the filtering element 12.

An insulated electrical conductor 29 may serve as a conducting means for transmitting RF current from the RF generator 30 to the first electrode 21 of the bipolar electrode means 66. The returning electrical conductor 22 from the second electrode 26 of the bipolar electrode means 66 is connected to an external RF generator 30.

Figure 5:
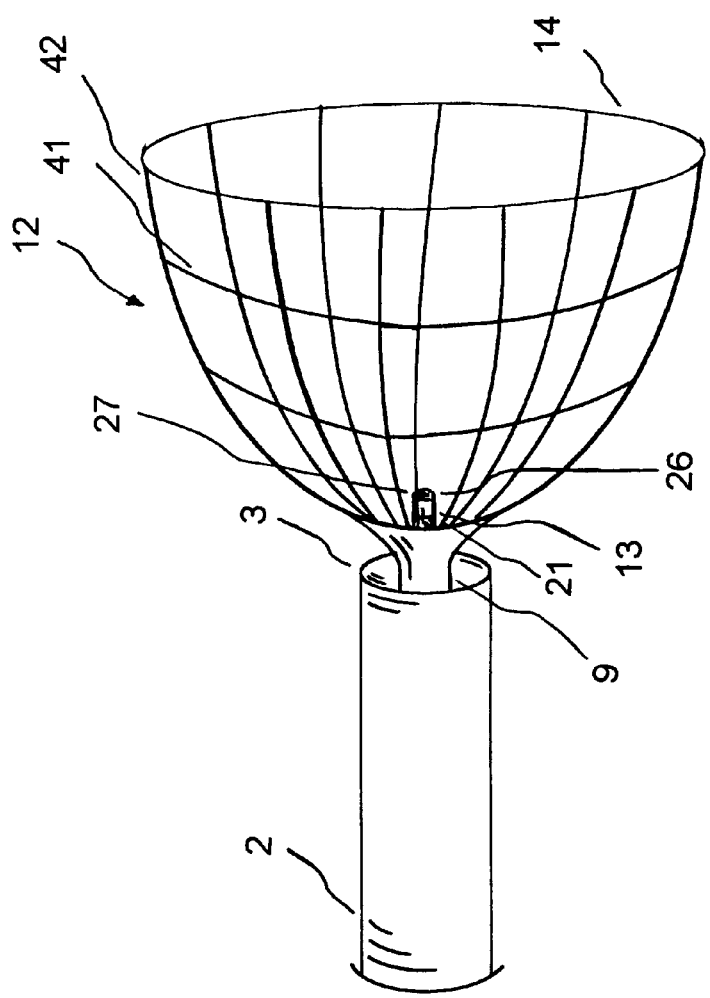
FIG. 5 is a perspective view of the distal end portion of FIG. 4, showing the filtering element and a bipolar electrode means for treating the trapped biological debris.

FIG. 5 shows a perspective view of the distal end portion of FIG. 4, showing the filtering element 12 and a bipolar electrode means 66 for treating the trapped biological debris. The bipolar electrode 66 may comprises a first electrode 21 and a second electrode 26, separated by an insulating zone 13. The filtering element 12 may comprise a plurality of longitudinally supporting elements 41 and a plurality of transverse supporting elements 42 so that a filtering net means is formed by said elements 41 and 42. A periphery 14 of the filtering element 12 is formed from the elements 41 and 42 for contacting the biological vessel and defining the filtering channel. The filtering channel defined by said filtering element 12 and its periphery 14 is at least as large as a diameter of the biological vessel. The filtering element 12 may form a generally frustoconical shape. Said filtering element 12 is generally expanding in the distal direction away from said delivery catheter 2. In a preferred embodiment, an exterior surface of the filtering element 12 is electrically non-conductive.

In one embodiment, the filter system comprises at least one temperature sensor 27 for measuring temperature of the entrapped biological debris 25, wherein the temperature sensor 27 is preferably disposed at close proximity of the bipolar electrode means 66 or other debris treatment means. The filter system further comprises a temperature controller 23, wherein the temperature measured from the at least one temperature sensor is relayed to said temperature controller, the temperature controller being adapted for effecting RF current delivery to the bipolar electrode means 66. When the measured temperature rises to a preset high-limit point, the temperature control mechanism sends out a signal to cut off the RF current supply. In a similar manner, when the measured temperature drops to a preset low-limit point, the temperature control mechanism sends out a signal to activate the RF current supplies.

Figure 6:
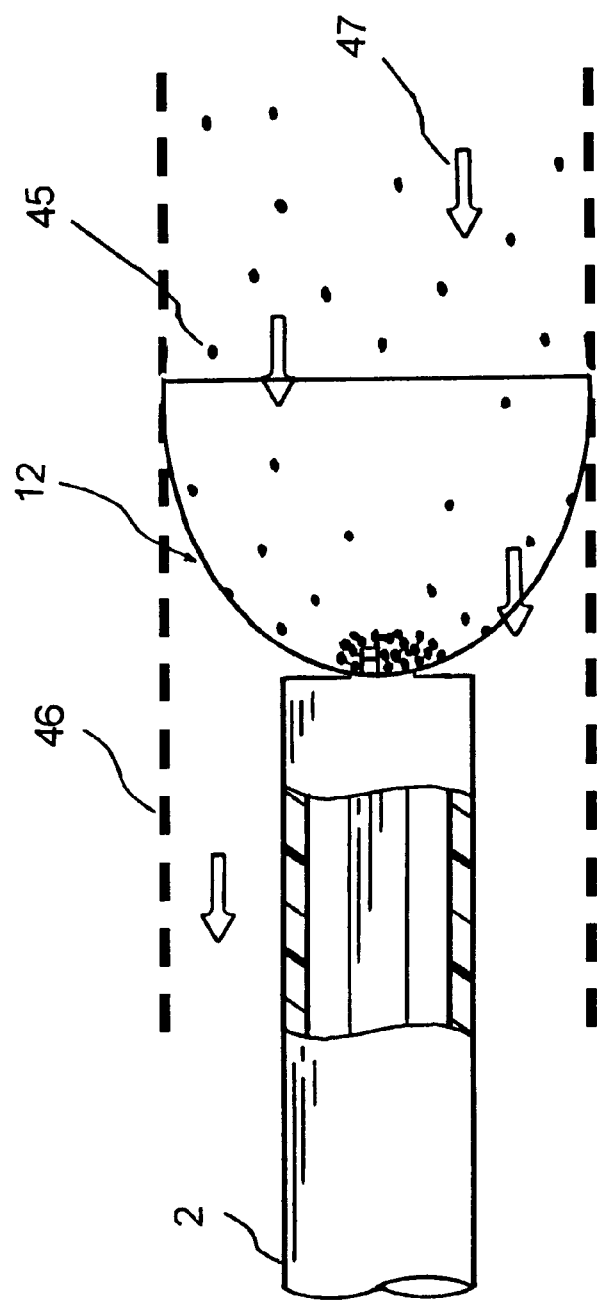
FIG. 6 is an illustrative view of the debris being entrapped by a filtering element and treated by a debris treatment means of FIG. 4 of the present invention.

FIG. 6 shows an illustrative view of a collection of individual debris 45 being entrapped by a filtering element 12 and treated by a debris treatment means of FIG. 4 of the present invention. The debris treatment means may be selected from the group consisting of a radiofrequency bipolar electrode, an ultrasound transducer, a plurality of laser fiber optics, a microwave antenna, a mechanical compressor, and a mechanical cutter. The periphery of the filtering element 12 contacts a biological vessel 46, such as a blood vessel. Each of the debris 45 flow in the blood direction 47 which approaches the distal end of the filtering element 12 from the far distal sources. The debris 45 tends to be entrapped at a proximal end of the filtering element 12, whereby a debris treating means is located to treat the collection of debris 25.

Figure 7:
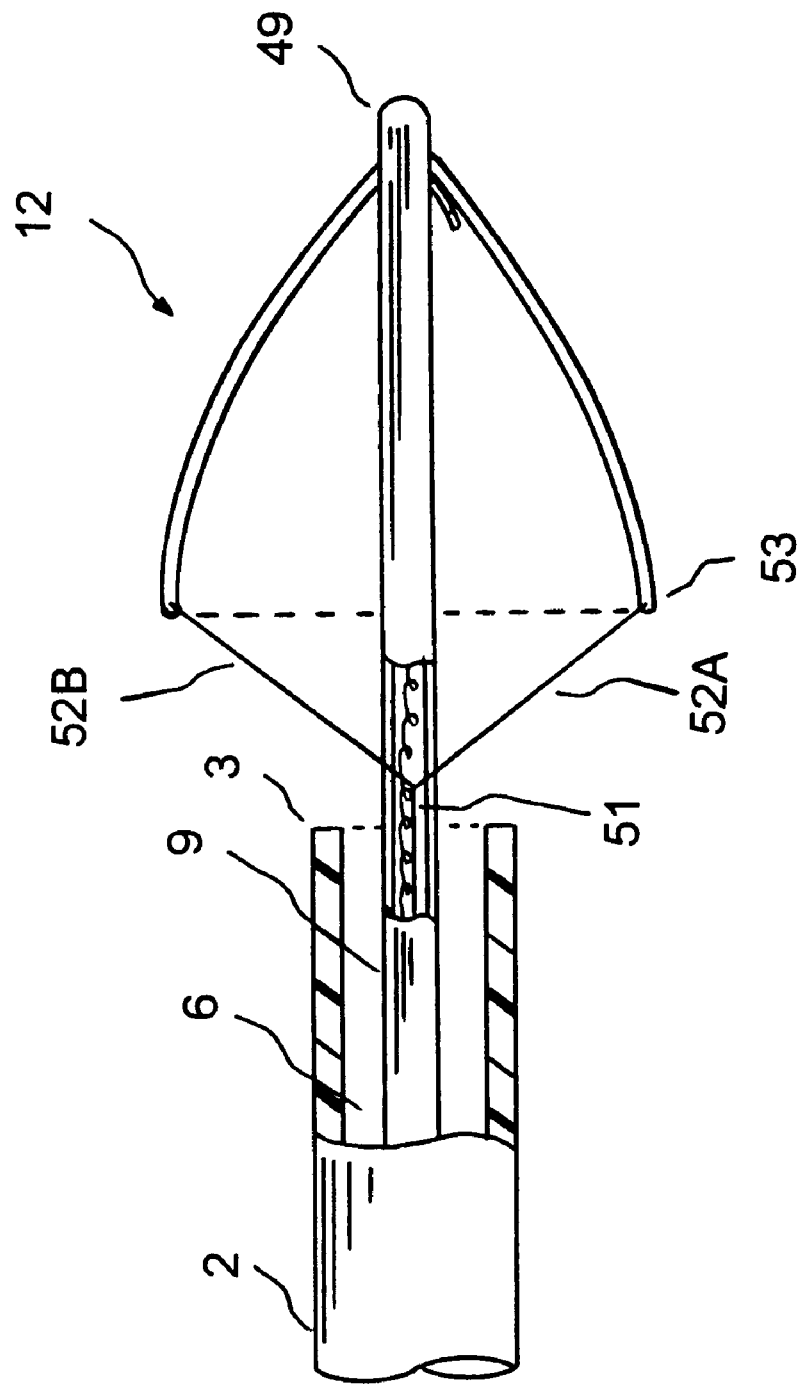
FIG. 7 is a cross-sectional view of the distal end portion of another preferred delivery catheter, having a deployable filter element that is deployed at a deployed state.
Figure 8:
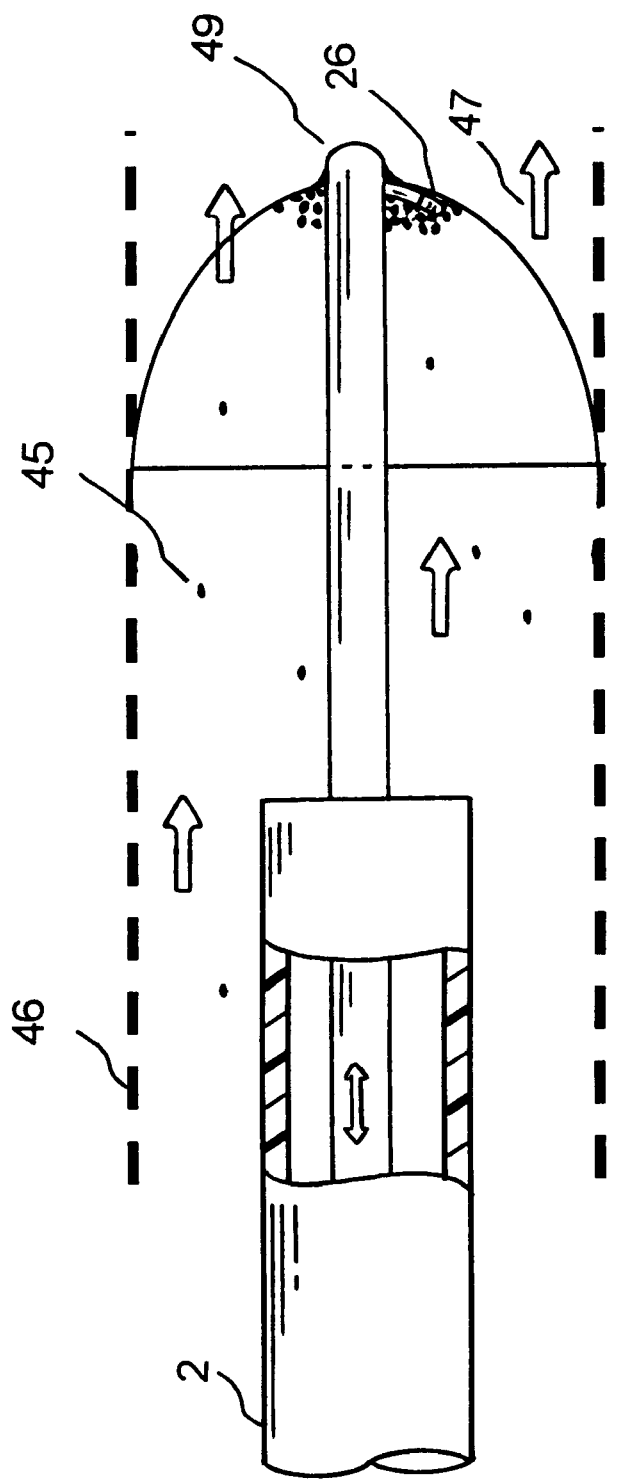
FIG. 8 is an illustrative view of the debris being entrapped by a filtering element and treated by a debris treatment means of FIG. 7 of the present invention.

For a fluid flowing in parallel to the delivery catheter 2 as shown in FIGS. 7 and 8, a cross-sectional view of the distal end portion of another preferred delivery catheter 2 is illustrated. The delivery catheter 2 has a deployable filter element 12 at a deployed state. When said filtering element 12 is deployed, the filtering element defines a filtering channel that extends radially outwardly so that a cross-sectional area of the biological vessel 46 is essentially covered by a periphery 14 of said filtering channel. The deployment of the filtering element 12 may be accomplished by a filter deployment means 20. In one embodiment, a plurality of deployment wires 52A, 52B is deployed from the filter deployment means 20 to expand the filtering element 12 at a deployed state. At a non-deployed state, the plurality of deployment wires 52A, 52B may be pulled by a central deployment wire 51 which proximal end is connected all the way to the filter deployment means 20 at the handle 8 so that the ends 53 of the filtering element 12 can be retracted into the lumen 6 of the delivery catheter 2.

FIG. 8 shows an illustrative view of a plurality of debris 45 being entrapped by a filtering element 12 and treated by a debris treatment means of FIG. 7 of the present invention. The debris treatment means may be selected from the group consisting of a radiofrequency bipolar electrode, an ultrasound transducer, a plurality of laser fiber optics, a microwave antenna, a mechanical compressor, and a mechanical cutter.

The periphery of the filtering element 12 contacts a biological vessel 46, such as a blood vessel. Each of the debris 45 flows in the blood direction 47 which approaches the distal end of the filtering element 12 from the proximal end of the debris sources. The debris 45 tends to be entrapped at the distal end of the filtering element 12, whereby a debris treating means is located.

A method for filtering and treating emboli from blood within a blood vessel, the method comprising the steps of: (a) introducing a delivery catheter into the blood vessel, the delivery catheter having a distal section, a distal end, a proximal end, and at least one lumen extending between the distal end and the proximal end, wherein the at least one lumen has at least one opening at the distal end of the delivery catheter; a handle attached to the proximal end of the delivery catheter, wherein the handle has a cavity; a retractable elongate element located inside the at least one lumen of the delivery catheter, said elongate element having a distal end and a proximal end; filter device means for filtering fluid within the biological vessel, wherein the filter device means comprises an emboli treatment means for reducing a size of the emboli and a filtering element, the filter device means being mounted at the distal end of the elongate element, the filtering element being made of shape memory material and being formed to have a pre-disposed shape which, when said filtering element is deployed, defines a filtering channel that extends radially outwardly so that a cross-sectional area of the biological vessel is essentially covered by a periphery of said filtering channel; a filter deployment means mounted on the handle, the filter deployment means being attached to the proximal end of the elongate element, wherein the elongate element is pushed distally, at a deployed state of the filter deployment means, so that the filtering element is fully deployed out of the at least one lumen of the delivery catheter and so that the emboli are trapped within the filtering element; (b) advancing the distal end of the delivery catheter to a desired location within the blood vessel; and (c) advancing the filtering element relative to the delivery catheter so that the filtering element deploys out of the at least one lumen of the delivery catheter and expands into its pre-disposed shape within the blood vessel for trapping the emboli. In a preferred embodiment, the emboli treatment means is selected from the group consisting of a radiofrequency bipolar electrode, an ultrasound transducer, a plurality of laser fiber optics, a microwave antenna, a mechanical compressor, and a mechanical cutter.

In a particular embodiment, the material for the bipolar electrode means of this invention consists of conductive metals such as platinum, iridium, gold, silver, stainless steel, Nitinol, tungsten, or an alloy of these metals.

From the foregoing description, it should now be appreciated that a filter system for filtering biological debris, comprising a filtering element and a suitable debris treatment means has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A filter system within a biological vessel comprising:
   a delivery catheter having a distal section, a distal end, a proximal end, and at least one lumen extending between the distal end and the proximal end, wherein the at least one lumen has at least one opening at the distal end of the delivery catheter;
   a handle attached to the proximal end of the delivery catheter, wherein the handle has a cavity and wherein a filter deployment means is mounted on the handle;
   a retractable elongate element located inside the at least one lumen of the delivery catheter, said elongate element having a distal end and a proximal end, wherein the filter deployment means is coupled to the proximal end of the elongate element;
   filter device means for filtering fluid within the biological vessel, wherein the filter device means comprises a bipolar electrode means and a filtering element, the filter device means being coupled to the distal end of the elongate element, the filtering element being made of shape memory material and being formed to have a pre-disposed shape which, when said filtering element is deployed, defines a filtering channel that extends radially outwardly so that a cross-sectional area of the biological vessel is essentially covered by a periphery of said filtering channel;
   the elongate element being adapted to be pushed outwardly distally from the handle, at a deployed state of the filter deployment means, so that the filtering element is fully deployed out of the at least one lumen of the delivery catheter and so that biological debris are trapped within the filtering element; and
   a RF current generator, wherein a RF current is delivered to the bipolar electrode means through a forwarding electrical conductor to a first electrode of the bipolar electrode means, and wherein the RF current returns from a second electrode of the bipolar electrode means through a returning electrical conductor to the RF current generator to form a complete circuit.

2. The filter system within a biological vessel of claim 1, wherein the biological vessel is a blood vessel.

3. The filter system within a biological vessel of claim 1, wherein said filtering element forms a generally frustoconical shape.

4. The filter system within a biological vessel of claim 1, wherein said filtering element is generally expanding in the distal direction away from said delivery catheter.

5. The filter system within a biological vessel of claim 1, wherein the filtering channel defined by said filtering element is at least as large as a diameter of the biological vessel.

6. The filter system within a biological vessel of claim 1, wherein the biological debris is selected from the group consisting of blood clots, emboli, and loosen biological debris.

7. The filter system within a biological vessel of claim 1, wherein the filtering element is shaped either concave or convex with reference to a central axial line when the filtering element is deployed.

8. The filter system within a biological vessel as in claim 1 further comprising at least one temperature sensor for measuring temperature of the trapped biological debris, wherein the temperature sensor is preferably disposed at close proximity of the bipolar electrode means.

9. The filter system within a biological vessel as in claim 8 further comprising a temperature controller, wherein the temperature measured from the at least one temperature sensor is relayed to said temperature controller, the temperature controller being adapted for effecting RF current delivery to the bipolar electrode means.

10. The filter system within a biological vessel of claim 1, wherein the RF current varies within the range of 50 to 2,000 kHz.

11. The filter system within a biological vessel of claim 1, wherein an exterior surface of the filtering element is electrically non-conductive.

12. A filter system within a biological vessel comprising:
a delivery catheter having a distal section, a distal end, a proximal end, and at least one lumen extending between the distal end and the proximal end, wherein the at least one lumen has at least one opening at the distal end of the delivery catheter;
a handle attached to the proximal end of the delivery catheter, wherein the handle has a cavity and wherein a filter deployment means is mounted on the handle;
a retractable elongate element located inside the at least one lumen of the delivery catheter, said elongate element having a distal end and a proximal end, wherein the filter deployment means is coupled to the proximal end of the elongate element;
filter device means for filtering fluid within the biological vessel, wherein the filter device means comprises a debris treatment means for treating biological debris and a filtering element, the filter device means being coupled to the distal end of the elongate element, the filtering element being made of shape memory material and being formed to have a pre-disposed shape which, when said filtering element is deployed, defines a filtering channel that extends radially outwardly so that a cross-sectional area of the biological vessel is essentially covered by a periphery of said filtering channel;
the elongate element being adapted to be pushed outwardly distally from the handle, at a deployed state of the filter deployment means, so that the filtering element is fully deployed out of the at least one lumen of the delivery catheter and so that the biological debris are trapped within the filtering element; and
the debris treating means being selected from the group consisting of an ultrasound transducer, a plurality of laser fiber optics, a microwave antenna, a mechanical compressor, and a mechanical cutter.

13. The filter system within a biological vessel of claim 12, wherein the biological vessel is a blood vessel.

14. The filter system within a biological vessel of claim 12 wherein said filtering element forms a generally frustoconical shape.

15. The filter system within a biological vessel of claim 12, wherein the biological debris is selected from the group consisting of blood clots, emboli, and loosen biological debris.

16. A method for filtering and treating emboli from blood within a blood vessel, the method comprising the steps of:
(a) introducing a delivery catheter into the blood vessel, the delivery catheter having a distal section, a distal end, a proximal end, and at least one lumen extending between the distal end and the proximal end, wherein the at least one lumen has at least one opening at the distal end of the delivery catheter;
a handle attached to the proximal end of the delivery catheter, wherein the handle has a cavity and wherein a filter deployment means is mounted on the handle;
a retractable elongate element located inside the at least one lumen of the delivery catheter, said elongate element having a distal end and a proximal end, wherein the filter deployment means is coupled to the proximal end of the elongate element;
filter device means for filtering fluid within the biological vessel, wherein the filter device means comprises an emboli treatment means for reducing a size of the emboli and a filtering element, the filter device means being coupled to the distal end of the elongate element, the filtering element being made of shape memory material and being formed to have a pre-disposed shape which, when said filtering element is deployed, defines a filtering channel that extends radially outwardly so that a cross-sectional area of the biological vessel is essentially covered by a periphery of said filtering channel;
the elongate element being adapted to be pushed outwardly distally from the handle, at a deployed state of the filter deployment means, so that the filtering element is fully deployed out of the at least one lumen of the delivery catheter and so that the biological debris are trapped within the filtering element;
(b) advancing the distal end of the delivery catheter to a desired location within the blood vessel;
(c) advancing the filtering element relative to the delivery catheter so that the filtering element deploys out of the at least one lumen of the delivery catheter and expands into its pre-disposed shape within the blood vessel for trapping the emboli; and
(d) treating the entrapped emboli, wherein the debris treating means is selected from the group consisting of a radiofrequency bipolar electrode, an ultrasound transducer, a plurality of laser fiber optics, a microwave antenna, a mechanical compressor, and a mechanical cutter.

17. The method for filtering and treating emboli from blood within a blood vessel as in claim 16, wherein the delivery catheter further comprises at least one temperature sensor for measuring temperature of the trapped emboli, wherein the temperature sensor is preferably disposed at close proximity of the emboli treatment means.

18. The method for filtering and treating emboli from blood within a blood vessel as in claim 16, where an exterior surface of the filtering element is electrically non-conductive.

* * * * *